BIS(SULFIDE)GOLD(1+) SALTS

This invention relates to new bis(sulfide)gold(1+) salts. These compounds have antiarthritic activity and, in particular, are of use in the treatment of rheumatoid arthritis.

The compounds of this invention are represented by the following formula:

FORMULA I

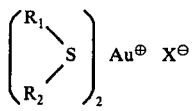

in which $R_1$ and $R_2$ are 2-hydroxyethyl or taken together with the sulfur atom to which they are attached form a tetrahydrothienyl or tetrahydrothiapyranyl ring and X is a weakly nucleophilic anion.

A particular compound of this invention is represented by Formula I in which $R_1$ and $R_2$ taken together with the sulfur atom to which they are attached form a tetrahydrothienyl ring.

The anion X in Formula I is a weakly nucleophilic anion such as, for example, perchlorate ($ClO_4$), iodate ($IO_4$), tetrafluoroborate ($BF_4$) and hexafluorophosphate ($PF_6$).

The compounds of this invention are prepared by the following procedure:

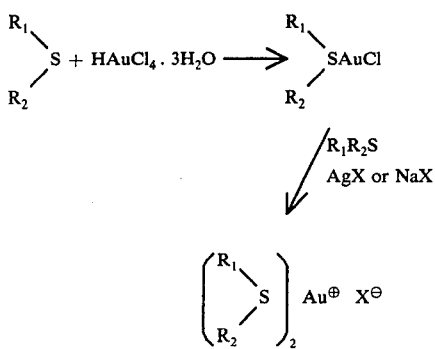

The terms $R_1$, $R_2$ and X are as defined above.

According to the above procedure, a sulfide, $R_1R_2S$, is reacted with gold acid chloride trihydrate to give the chloro(sulfide)gold compound $R_1R_2SAuCl$. This reaction is carried out in a suitable solvent, such as aqueous ethanol, conveniently at room temperature. The chloro(sulfide)gold compound is reacted with a silver salt AgX or a sodium salt NaX and a sulfide $R_1R_2S$. This reaction is carried out in a solvent, such as acetone, at room temperature. The products are the bis(sulfide)-gold(1+) salts of this invention.

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 mg. of *Mycobacterium butyricum* suspended in white paraffin oil into the left hindpaw footpad. The injected paw becomes inflamed (increased volume) and reaches maximal size within 3 to 5 days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg. to about 10 mg.

The method of producing antiarthritic activity by administering internally to an animal a compound of Formula I is also an object of this invention. The compounds of Formula I are administered in an amount sufficient to produce antiarthritic activity. The route of administration may be orally or parenterally, preferably orally. Advantageously, doses will be administered 1 or 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

A solution of 4.0 g. (0.045 mole) of tetrahydrothiophene in 15 ml. of ethanol was added dropwise to a solution of 5.0 g. (0.013 mole) of gold acid chloride

United States Patent [19]
Hill

[11] 4,112,113
[45] Sep. 5, 1978

[54] BIS(SULFIDE)GOLD(1+) SALTS

[75] Inventor: David T. Hill, North Wales, Pa.

[73] Assignee: SmithKline Corporation, Philadelphia, Pa.

[21] Appl. No.: 772,034

[22] Filed: Feb. 25, 1977

[51] Int. Cl.² .................... A01N 9/00; C07D 327/00; C07D 333/00

[52] U.S. Cl. ............................ 424/275; 260/327 TH; 260/329 ME; 260/430; 424/290

[58] Field of Search ................. 260/329 ME, 327 TH; 424/275, 290

[56] References Cited

PUBLICATIONS

Hartough, "Thiophene and Its Derivatives", (1952), p. 456.

*Primary Examiner*—A. Siegel
*Attorney, Agent, or Firm*—Joan S. Keps; Richard D. Foggio; William H. Edgerton

[57] ABSTRACT

The compounds are bis(sulfide)gold(1+) salts which have antiarthritic activity.

4 Claims, No Drawings